United States Patent [19]

Hayaishi et al.

[11] Patent Number: 4,880,742
[45] Date of Patent: Nov. 14, 1989

[54] PROSTAGLANDIN BIOSYNTHESIS INHIBITORS

[75] Inventors: Osamu Hayaishi; Ryuji Ueno, both of Kyoto; Sachiko Kuno, Ibaraki, all of Japan

[73] Assignees: Research Development Corporation of Japan, Tokyo; Ueno Seiyaku Kabushikikaisha, Osaka, both of Japan

[21] Appl. No.: 10,519

[22] Filed: Feb. 3, 1987

[30] Foreign Application Priority Data

Feb. 14, 1986 [JP] Japan .................................. 61-31248

[51] Int. Cl.⁴ ........................ C12N 7/00; A61K 31/19
[52] U.S. Cl. ................................ 435/238; 435/240.2; 514/567
[58] Field of Search ........................... 514/2, 21, 567; 435/238, 240.2

[56] References Cited

PUBLICATIONS

Valone et al, J. Clinical Immunol., vol. 4, No. 5 (1984), pp. 383–387.
Skotnicki, cited in Chem. Abstracts, vol. 104:107715e, 1986.
Kuno et al, cited in Chem. Abstracts, vol. 105:19376k, 1986.
Bettini et al, cited in Biol. Abstracts, 82(4)37736, 1986.
Blackwell et al, Nature, vol. 287 (1980), pp. 147–149.
Amman, Chapter 22 of Basic and Clinical Immunology, 5th Ed., Stites et al, eds, (1984), pp. 418–419.
Kuno, S., et al, Proc. Natl. Acad. Sci., USA, 83, 3487–3490 (1986).
Shen, T. Y., J. Med. Chem., 24(1), 1–5 (1981).

*Primary Examiner*—Jacqueline M. Stone

[57] ABSTRACT

A method of treatment of the diseases caused by AIDS virus which comprises administering an effective amount of prostaglandin biosynthesis inhibitor to a subject in need of such treatment.

1 Claim, 2 Drawing Sheets

PROSTAGLANDIN BIOSYNTHESIS INHIBITORS

FIELD OF THE INVENTION

The present invention relates to a use of prostaglandin biosynthesis inhibitors for prevention, therapy, etc. of AIDS (acquired immunodeficiency syndrome). More particularly, the present invention provides a medicament containing a prostaglandin biosynthesis inhibitor as an active ingredient and a method of prevention and therapy of AIDS.

BACKGROUND OF THE INVENTION

World-wide interests have been focused on AIDS due to its unfavorable prognosis. It is a clinical syndrome known to occur more frequently among the male homosexualists, and is characterized by the clinical syndromes such as pnemocystis carinii pneuomonia, Kaposi's sarcoma, etc. and induces a high mortality of more than 70% by the dysregulation of immune system. It is also known that helper-T cells are specifically destroyed by the infection of the AIDS virus (e.g. HTLV-III).

As a result of the extensive study on the properties of the AIDS viruses, the present inventors have found out the fact that prostaglandins $E_2$ and $D_2$ have an action to accelerate, proliferation of AIDS virus (Proc. Natl. Acad. Sci. USA, 83, 3487–3490, May, 1986). In view of this fact, the present inventors have thought of a possibility that the proliferation of AIDS viruses could possibly be inhibited by inhibiting, conversely, the biosynthesis of prostaglandins.

Based on the above thought, the present inventors have conducted an experiment to uncover whether Diclofenac sodium, one of the non-steroidal anti-inflammatory substances, would inhibit proliferation of AIDS viruses. As a result, it has been confirmed that the production of virus is inhibited in vitro when the above substances are incubated with the AIDS virus producing cells. It has also been confirmed that the other non-steroidal anti-inflammatory substances exhibit the similar activities. The present invention has been completed on the basis of such findings.

RELATED DISCLOSURES

It is well known that prostaglandins are biosynthesized in a living body from arachidonic acid which is released from arachidonic acid-fatty acid phospholipoglyceride by phospholipase, and which is cyclized by the action of cyclooxygenase to form prostaglandins. The over-all process of biosynthesis of prostaglandins and related compounds is called "arachidonic acid cascade" (see Kirk-Othmer Encyclopedia of Chemical Technology, 3rd Ed., Supplement Volume, pages 714–719, John Willy & Sons, New York, U.S.A.). It is also known that the latter process, i.e., the change from arachidonic acid to prostaglandins, is inhibited by the non-steroidal anti-inflammatory substances (see. for example, Modern Chemistry (Gendai Kagaku), Extra Edition 1, "Prostaglandins And Pathema" (Purosutaguranzin To Byotai) pages 29 and 52).

SUMMARY OF THE INVENTION

In one aspect, the present invention provides a method of treatment of the disease caused by AIDS virus which comprises administering an effective amount of prostaglandin biosynthesis inhibitor to a subject in need of such treatment.

In another aspect, the present invention provides a use of prostaglandin biosynthesis inhibitor for the manufacture of a medicament for treatment of the diseases caused by AIDS virus.

In a further aspect, the present invention provides a pharmaceutical composition comprising a prostaglandin synthesis inhibitor as an active ingredient in association with a pharmaceutically acceptable carrier, diluent or excipient.

DETAILED DESCRIPTION AND PREFERRED EMBODIMENT

Figure 1:
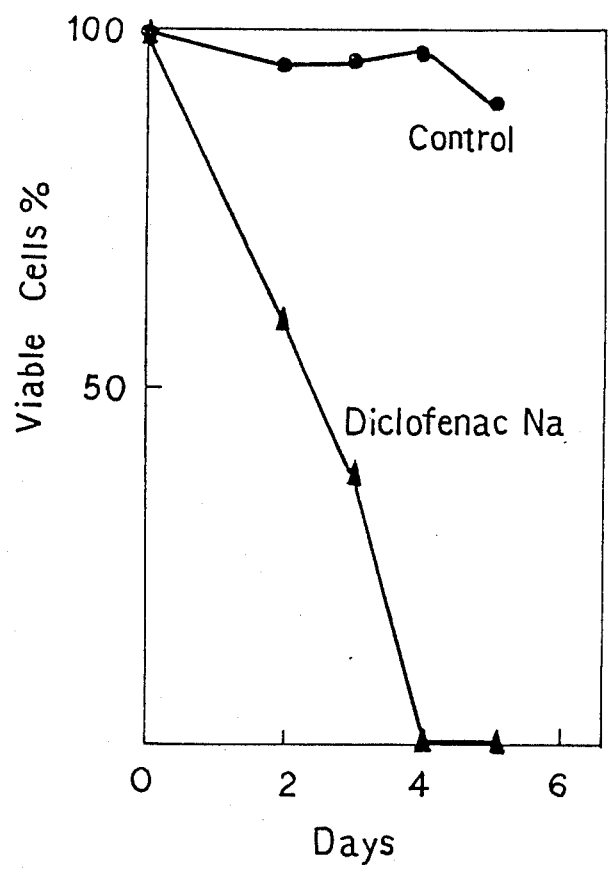
FIGS. 1 and 2 show the viable cells (%) of the AIDS virus infected established cell line Molt-4/HTLV-III cells and the non-infected established cell line Molt-4 cells, respectively, with or without addition of Diclofenac sodium.

The term "treatment" herein is intended to cover all controls of disease including prevention, sustention (i.e. prevention of aggravation), reducing (i.e. alleviation of conditions) and therapy.

The term "AIDS" is intended to cover all diseases resulted from the infection of so-called AIDS viruses (e.g. HTLV-III, LAV1, LAV2, ARV).

In the biosynthesis of prostaglandins (to be abbreviated as PG), it is known that arachidonic acid is converted firstly into $PGG_2$ by the action of cyclooxygenase, and said $PGG_2$ in turn is changed into $PGH_2$ and further to $PGD_2$, $PGE_2$, $PHI_2$, etc. Therefore, if the first step of this cascade is inhibited, the biosynthesis of prostaglandins would be entirely inhibited. Accordingly, the term "prostaglandins" to be referred to in the phrase "prostaglandin biosynthesis inhibitor(s)" used herein is intended to include all prostaglandins which may be biologically synthesized.

The term "prostaglandin bisoynthesis inhibitors" used herein includes compounds which inhibit the formation of arachidonic acid from arachidonic acid glyceride (phospholipase inhibitor) and those which inhibit the formation of prostaglandin from arachidonic acid. The former includes lipomodulin (also known as macrocortin, or lipocortin), a kind of protein, and the latter includes a non-steroidal anti-inflammatory substances (especially those which are acidic). Specific examples of the latter are salicyclic acid derivatives such as Aspirin, salicyl salicylic acid, DL-lysine monoacetyl salicylate, etc., pyrazolone derivatives such as Phenopyrazone, Nifenazone, Phenylbutazone, Oxyphenbutazone, Ketophenylbutazone, Clofezone, Difenamizole, etc., anthranylic acid derivatives such as Mefenamic acid, Fulfenamic acid, Niflumic acid, etc., phenyl acetic acid derivatives such as Diclofenac, Ibufenac, Ibuprofen, Alclofenac, Ketoprofen, Fenbufen, Flurbiprofen, etc., indol or indazole derivatives such as Indomethacin, Sulindac, Benzydamine, etc., and further Naproxen, Tiaramide, Bucolome, Metopyrimzaole, Azapropazone, etc. and their salts.

The dosage of the above prostaglandin biosynthesis inhibitor to be administered may be approximately the same as that used generally in the anti-inflammatory therapy. For example for salicylic acid agent, 0.5–5 g/day, for pyrazolone derivative, 0.1–2 g/day, for anthranylic acid derivative, 0.3–2 g/day, for phenyl acetic acid derivative, 0.2–3 g/day, and for indole derivative, 0.2–2 g/day, may be administered in 1–4 divisions a day, or as a sustained release formulation. The administration route may optional such as peroral, rectal, injection, etc. and suitably selected according to effective ingredient.

For administration, the effective ingredient may be mixed with a pharamceutical carrier such as organic or inorganic solid or liquid excipient, e.g., suitable for oral administration, intrarectal administration, injection, etc. and administered in the form of the conventional pharmaceutical preparation. Such preparation includes solids (e.g., tablet, granule, powder, capsule, etc.) and liquids (e.g., liquid, emulsion, suspension, etc.). The above carriers include starch, lactose, glucose, sucrose, dextran, cellulose, paraffin, fatty acid glyceride, water, alcohol, gum arabic, etc. If necessary, auxiliary, stabilizer, wetting agent, emulsifier, lubricant, binder, and other conventional additives may be added.

The present invention is illustrated in further detail by way of Examples.

EXAMPLE 1

| Diclofenac sodium | 25 mg |
| --- | --- |
| Magnesium stearate | 5 mg |
| Corn starch | 20 mg |
| Lactose | 150 mg |

The above ingredients are mixed and pressed into tablets according to the conventional procedure.

EXAMPLE 2

| Indomethacin | 25 mg |
| --- | --- |
| Magnesium stearate | 2 mg |
| Lactose | 223 mg |

The above ingredients are mixed and filled in hard gelatine capsules.

EXAMPLE 3

| Oxyphenbutazone | 50 mg |
| --- | --- |
| Fatty acid glyceride | 1950 mg |

The above ingredients are melted and mixed according to the conventional procedure to make suppositories.

EXAMPLE 4

| Mefenamic acid | 250 mg |
| --- | --- |
| Magnesium stearate | 5 mg |
| Lactose | 230 mg |
| Corn starch | 15 mg |

The above ingredients are mixed and filled in hard gelatine capsules.

EXAMPLE 5

| DL-Lysine monoacetyl salicylate | 900 mg |
| --- | --- |
| Glycine | 100 mg |
| Calcium chloride | 50 mg |

The above ingredients are filled in vials according to the conventional procedure to make intravenous injections.

EXAMPLE 6

Figure 2:
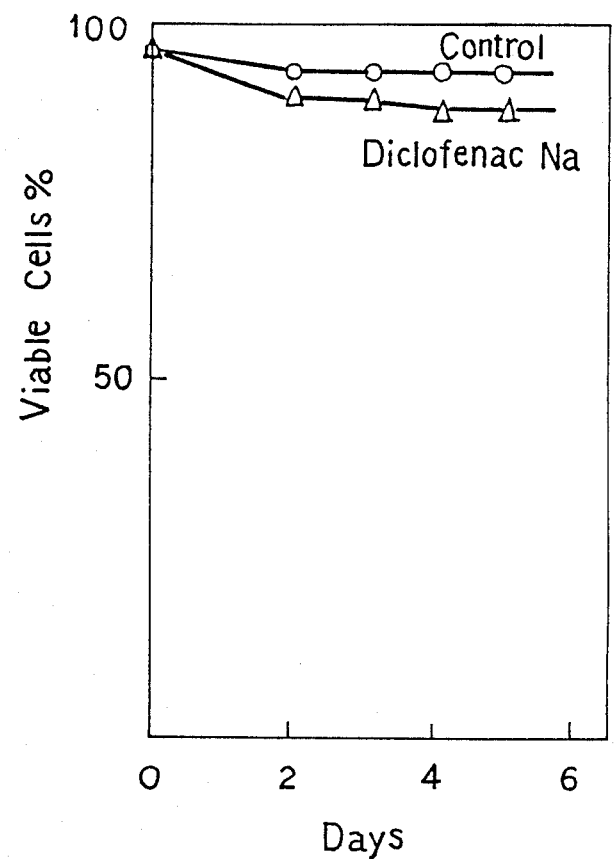

The cell line Molt-4, established from the lymphocytes of a patient of human acute lymphatic leukemia is susceptible to HTLV-III, and the cell line Molt-4/HTLV-III, established from Molt-4 cells infected with HTLV-III, can continuously produce viruses during the cell proliferation. These viral producer cells Molt-4/HTLV-III, were cultured in a medium containing 100 $\mu$M Diclofenac sodium. In this experiment, the viability of the viral producer cells decreased markedly and on day 4 almost all cells were killed as shown in FIG. 1. In a control without Diclofenac sodium, scarce change was seen in cell viability. In contrast to the results shown in FIG. 1, FIG. 2 indicated that the viability of Molt-4 cells (HTLV-III uninfected) was not changed irrespective of presence or absence of Diclofenac sodium.

The above results elucidate that Diclofenac sodium shows cytotoxicity specifically to the cells infected with AIDS virus, and accordingly is usable for the treatment of AIDS.

What is claimed is:

1. A method of inhibiting proliferation of AIDS-virus producer human T-cells which comprises providing in the presence of such cells Diclofenac or a pharmaceutically acceptable salt thereof in amount cytocidally effective in response to said producer human T-cells but ineffective in respect to normal human T-cells.

* * * * *